United States Patent [19]
Johal

[11] 4,400,471
[45] * Aug. 23, 1983

[54] PREPARATION AND CRYSTALLIZATION OF FRACTION I PROTEIN FROM PLANT SOURCES

[76] Inventor: Sarjit S. Johal, 1411 S. 11th St., Lincoln, Nebr. 68502

[*] Notice: The portion of the term of this patent subsequent to Jun. 8, 1999 has been disclaimed.

[21] Appl. No.: 312,194

[22] Filed: Oct. 19, 1981

Related U.S. Application Data

[63] Continuation-in-part of Ser. No. 203,779, Nov. 3, 1980, Pat. No. 4,334,024.

[51] Int. Cl.$^3$ ............................................. C12N 9/88
[52] U.S. Cl. .................................... 435/232; 435/815
[58] Field of Search ............................... 435/232, 815

[56] References Cited

U.S. PATENT DOCUMENTS

| | | | |
|---|---|---|---|
| 4,268,632 | 5/1981 | Wildman et al. | 435/232 |
| 4,340,676 | 7/1982 | Bourque | 435/232 |
| 4,347,324 | 8/1982 | Wildman et al. | 435/232 |

OTHER PUBLICATIONS

Paulsen et al., Biochemistry, vol. 5, No. 7.
Johal et al., Science, vol. 204, Apr. 6, 1979, pp. 75 to 77.

*Primary Examiner*—Lionel M. Shapiro
*Attorney, Agent, or Firm*—Townsend & Townsend

[57] ABSTRACT

A method for the purification of ribulose 1,5-bisphosphate carboxylase (RuBisCO) to a greater than 90% purity from a wide variety of plant species is disclosed. The steps include comminuting and homogenizing a plant material, such as leaves, in aqueous solution. The solution is filtered and the residue discarded. After fractionation, sufficient polyethylene glycol (PEG) is added to bring the concentration of PEG in the range of from 8 to 13 (weight/volume) percent, causing precipitation of the RuBisCO. To enhance crystal formation, magnesium chloride can be added to the solution. As a purification step, or as an alternate (to crystallization) separation step, the RuBisCO may be applied to a strong basic ion-exchange resin. The RuBisCO is selectively eluted in the presence of a divalent metal ion, such as $Mg^{+2}$, $Ca^{+2}$ or $Zn^{+2}$.

14 Claims, No Drawings

PREPARATION AND CRYSTALLIZATION OF FRACTION I PROTEIN FROM PLANT SOURCES

BACKGROUND OF THE INVENTION

This is a continuation-in-part of pending prior application Ser. No. 203,779 for PREPARATION AND CRYSTALLIZATION OF FRACTION I PROTEIN FROM PLANT SOURCES filed on Nov. 3, 1980 by Sarjit S. Johal, now U.S. Pat. No. 4,334,024, issued June 8, 1982.

1. Field of the Invention

This invention relates to a method of preparing and crystallizing Fraction I protein directly from unpurified extracts of a variety of plant species.

With the cost and inefficiency involved in the production of animal protein for human consumption and with the steady growth of world population, and increased usage of protein resources, it is becoming more apparent that non-conventional sources must be tapped for the production of high quality proteins that meet industrial needs as well as the nutritional standards and requirements for both human and animal consumption. Within the last thirty or so years, as the need for new sources of high quality protein has become crucial, terrestrial and aquatic plants have been seriously investigated as possible protein sources. Leaves of all plants contain certain soluble proteins that are generally rich in the essential amino acids and thus offer a high potential for the increased production of high quality protein for human and animal dietary needs and at affordable prices.

It is well known in the art that considerable amounts of protein can be recovered from forage crops without destroying or decreasing their value as fodder or silage, by suitably modifying and improving available processing techniques. Under most current agricultural practices, however, valuable proteins obtainable from plants and forage crops are discarded and thus wasted.

In recent times, however, some techniques have been developed for the production of plant proteins. Such known techniques do not involve separating or identifying the nature, type and quality of the resulting proteins. Thus, such protein-rich products are in a form that is generally not of the highest quality and therefore unsuitable for human consumption. One such simple procedure for the preparation of a protein from the leaves of alfalfa consists of obtaining therefrom a dark green non-protein fraction that may be dried and used as animal fodder, and a white, bland, protein-rich fraction which is insoluble. Due to its insolubility, the protein-rich fraction is particularly unsuitable for human and animal consumption as a food additive or fortifier.

The most abundant major plant protein is Fraction 1 protein. Its major component has been identified as the enzyme ribulose 1,5-bisphosphate carboxylase (RuBisCO). Fraction 1 protein is widely distributed in nature and constitutes up to 50% of the soluble protein contained in leaves and approximately 20% of the total plant protein. The amino acid composition of Fraction 1 protein is well balanced in terms of the essential and non-essential amino acids, comparing favorably with soybean, casein and animal proteins. The amounts of the essential amino acids in Fraction 1 protein, with the exception of methionine, meet or even exceed standards established for human nutritional requirements. The protein also has potential utility in the medical field.

Before its usefulness and possible incorporation as a food supplement can be laboratory and field tested this major important protein must be isolated and purified in large quantities. It is essential that the protein be in a relatively pure form. However, current purification techniques are not applicable to large-scale isolation of RuBisCO in a pure form. Most published procedures for purifying Fraction 1 protein and its major component, RuBisCO, generally use small quantities of leaf tissue and require fairly elaborate analytical techniques such as ultracentrifugation and chromatography or sucrose gradient fractionation. While these procedures are useful for obtaining quantities of RuBisCO on a small laboratory scale sufficient for structural and enzymatic studies, they are incapable of purifying large quantities of the enzyme. It is physically impossible to scale-up most of these analytical methods to isolate and purify the enzyme in relatively pure form for its effective utilization in human and animal diets.

RuBisCO has also been crystallized, on the same analytical scale, using pre-purified extracts of seven plant species consisting of spinach, alfalfa, tomato, potato, corn, cotton, and tobacco. Such known methods have not been successful in the preparation of RuBisCO on a large, manufacturing scale nor have they been demonstrated to be effective in purifying the enzyme from unpurified extracts of plant species.

Currently only the RuBisCO from tobacco plants can be crystallized from unpurified extracts. The procedural steps heretofore used in the preparation of the crystalline tobacco enzyme involve the steps of (1) breaking the chloroplasts in the presence of high concentrations of sodium chloride to release the enzyme, (2) heating the resulting solution to precipitate all other undesirable components, (3) removing the excess sodium chloride by gel filtration, and (4) allowing the protein crystals to form.

However, crystallization is a complex phenomena and the molecular forces which cause proteins in general to crystallize are poorly understood. Solubility and viscosity properties of proteins differ from one protein to another and depend on the primary, secondary, tertiary (and where applicable), quaternary structures of the specific proteins. The nature and concentration of electrolytes present in the medium, the pH, temperature, and concentration of the protein are crucial factors which influence the crystallization process. The choice of the precipitant employed in initiating nucleation and crystallization of proteins also plays an important role.

The optimum concentrations of these various reactants which are effective for one protein may or may not be effective for other proteins, due to wide variations in their structures. In addition, proteins are very sensitive to heat and chemicals which can cause their denaturation. Each protein, or even the same protein derived from different species, may vary in their primary, secondary, and tertiary structures and generally must be studied separately and independently to determine their structural and chemical properties.

Existing procedures for the crystallization of tobacco RuBisCO, while a significant improvement over other earlier techniques, suffers many of the aforementioned drawbacks and is of limited utility. For instance the process can only be used successfully with tobacco leaves that are no more than 3-4 months old, such leaves being unavailable under current agricultural practices. All other sources of RuBisCO have proven unsatisfactory to crystallization by this procedure.

The need for gel filtration and the inherent limitations in using this step severely limit the total quantity of material processed. Furthermore the tobacco RuBisCO crystals obtained in this manner are not stable to lyophilization, which produces a powder that is insoluble, precluding its use in many formulations and as a food additive. Since the crystals have not been found to be capable of being freeze-dried, the nutritional value of the crystals may be diminished because 70% of the volume is aqueous. Storage and transfer may also become a problem.

Thus, there is a continual need for a method of preparation and crystallization of Fraction 1 protein and RuBisCO in sufficiently large quantities to enable its utilization as a major protein source for animal and human consumption.

2. Description of the Prior Art

U.S. Pat. No. 2,600,903 issued Mar. 26, 1948 to Miller disclosed a method for extracting alfalfa juice of high nutritional quality from freshly harvested alfalfa, involving adjusting the raw juice to an alkaline pH, concentrating and recovering the juice after separating the precipitated solids.

U.S. Pat. No. 3,780,183 issued Dec. 18, 1973, to Edwards teaches a method of preparing aqueous, alkaline solutions of alfalfa and clover, by subjecting the solution to digestion with pancreatin or a similar proteolytic enzyme and separating the soluble and insoluble portions, both of which have been found to have nutritional value.

U.S. Pat. No. 3,823,128 issued July 9, 1974 to Bickoff et al., discloses a method for the fractionation of alfalfa and other leafy green crops, for the isolation and purification of a protein fraction free from chlorophyll and other pigments, cellulose fibers and other components unsuitable for human consumption.

Paulsen and Lane, Biochemistry, 52,350 (1966) present a protocol for purifying spinach-bisphosphate-carboxylase in quantities sufficient for enzymatic studies.

Chan et al., [P. H. Chan, K. Sakano, S. Singh and S. G. Wildman], Science, 176, 1145 (1972) describe a method for crystallization of tobacco-bisphosphate-carboxylase using a low salt dialysis technique and partially purified enzyme as starting material.

Johal and Bourque, Science, 204, 75 (1979), reported crystallization of spinach Fraction 1 protein on an analytical and preparative scale using prepurified enzyme and an equilibrium vapor diffusion technique with polyethylene glycol as a precipitant.

Kung et al., [S. D. Kung, R. Chollet and T-V. Marsho], Methods of Enzymology, 69, 326 (1980) describe a simplified method for the crystallization and assay of tobacco ribulose-bisphosphate carboxylate-oxygenase.

SUMMARY OF THE INVENTION

The subject invention provides a method for the purification and crystallization of ribulose 1,5-bisphosphate carboxylate (RuBisCO) to a greater than 90% purity from a wide variety of plant species. The RuBisCO can be purified to form a product substantially free from impurities.

According to the subject method, plant material is comminuted in an aqueous solution to form a suspension. The suspension is then fractionated to release the RuBisCo from the plant material. The fractionating may be achieved either by heating the suspension or by chemical treatment. After fractionation the remaining plant material including the membranes, organelles, fibers and the like, are separated, typically by centrifugation. The RuBisCO may be removed from the supernatant either by crystallization, ion-exchange techniques, or a combination of both.

Crystallization may be induced by adding polyethylene glycol (PEG) to a final concentration in the range of from 8 to 15 (weight/volume) percent, preferably in the 11 to 13 weight percent range. To enhance crystal formation, a low concentration of magnesium chloride ($MgCl_2$), preferably in the range from 0.01 to 0.04 M may be added to the solution, although this is not necessary. The mixture is allowed to stand at a low temperature, preferably for approximately 6 to 8 hours at about 4° C., allowing the RuBisCO crystals form.

The crystalline RuBisCO may be further purified (i.e., the remaining proteins and contaminants removed) by passage through an anionic resin bed. It has been found that in the absence of a divalent metal ion, the RuBisCO and some other contaminants will bind to the resin. In the presence of such ion, however, only RuBisCO is released from the resin. Thus by passing the solution through such a resin, the RuBisCO is bound to the resin. The resin may then be washed to remove the unbound contaminants, and thereafter the resin may be washed with a divalent metal ion solution to recover only the RuBisCO therefrom. In this way, RuBisCO having a very high purity may be obtained. It is also possible to pass the RuBisCO solution through the resin in the presence of the divalent metal ion. In this way, the binding of the RuBisCO is prevented from the outset and only the contaminants are bound.

Alternatively, the RuBisCO may be recovered in an ion exchange column without prior crystallization. After fractionation and removal of the remaining plant material by centrifugation, the supernatant may be passed directly through an ion exchange resin equilibrated with water. As described above, the bed is then washed with water to remove unbound material and thereafter washed with a divalent metal ion solution to elute the RuBisCO. The RuBisCO may then be lyophilized to obtain substantially pure RuBisCO protein.

DESCRIPTION OF THE PREFERRED EMBODIMENT

According to the subject method, a sample of plant material, preferably leaves, is comminuted and homogenized in aqueous solution having low concentration (typically 0.01 M) of a reducing agent, such as sodium meta-bisulfite. The pH of the solution may vary widely in the range of 5.5 to greater than 8.0, although a pH below 7.0 is preferred.

The crude leaf homogenate so obtained may be fractionated to release the RuBisCO by any conventional process. Most simply, the homogenate can be exposed to heat, typically 37°–40° C. for approximately 10 minutes. Alternatively, fractionation of the homogenate may be chemically induced by any one of a variety of well-known agents, such as dextrans, ammonium sulfate, and various polymeric alcohols, including polyethylene glycol. It is preferred to induce fractionation using polyethylene glycol (PEG) since PEG (at a higher concentration) can act as a precipitant in a later step of the process. Sufficient PEG to bring the concentration to 8 weight/volume percent has been found adequate.

After fractionation, the homogenate is filtered and the residue is discarded. The filtrate is maintained at a cool temperature, preferably in the range 2° C. to 7° C.

Polyethylene glycol (PEG) in the molecular weight range of about 5000 to 7000, preferably 6000, is added to the filtrate to being the final concentration of PEG to at least about 8 (weight/volume) percent, preferably in the 8–13 (weight/volume) percent range and more preferably 11–13 (weight/volume) percent. Addition of magnesium chloride in the concentration range of 0.01 to 0.04 M, preferably 0.02 to 0.03 M, following the addition of PEG enhances crystal formation and yield.

The supernatant is stored at a temperature of about 4° C. from about 2–10 hours, preferably about 6 to 8 hours. Pure RuBisCo crystals which separate out are collected, washed and stored or lyophilized and stored.

The crystal preparation so obtained is homogeneous and has a carboxylase activity comparable to preparations made by other, more elaborate techniques. This technique has been successful in the preparation of RuBisCO from ryegrass, alfalfa, spinach, oats, peas, tomato, potato, *Moricandia arvensis* and tobacco and is applicable to other plant species as well. In addition, the leaves of several plant species can be combined and crystalline RuBisCO obtained by use of the subject matter.

Addition of PEG may be accomplished in two stages but a two-stage addition is not a critical factor in the crystallization process. However, the two-stage addition reduces centrifugation time and the "g" values employed. The initial addition also effectively precipitates membranes and organelles which may interfere with crystal yields. The final concentration of PEG is critical for the effective crystallization of RuBisCO. In particular, final PEG concentration less than 5 percent has been found to decrease crystal yields. The physical state of the plant or condition of the leaves and the origin of species, do not affect crystallization by the subject method.

The crystals obtained by the above-described steps may, at times, be relatively impure. The impurities can be removed by an additional ion-exchange step using diethylaminoethyl ether (DEAE) as the ion-exchange resin. It has been found that RuBisCO binds to a strongly basic anion material in the absence of divalent metal ions, but will not bind (or becomes unbound) in the presence of divalent metal ions, such as $Mg^{+2}$, $Ca^{+2}$, $Zn^{+2}$ and the like. Moreover, the interaction is very specific and only RuBisCO is affected by the presence of the ion.

Two variations of the purification step are contemplated. First, the RuBisCO in the supernatant may be applied to a DEAE-cellulose column (such as Whatman DEAE-52, DEAE-53 and Sigma DEAE-cellulose) or equivalent ion-exchange resin with water in the presence of a divalent metal ion (e.g. $MgCl_2$ in the concentration range from 0.01 M to 0.1 M) in which case the column binds the impurities while the RuBisCO is eluted from the column.

In the second variation, the RuBisCO supernatant is applied to the column in the absence of the divalent metal ion. In that case, both the RuBisCO and the impurities are bound by the resin. After washing with pure water, the RuBisCO can be specifically eluted by applying a metal ion solution to the column. Such solution is preferably in the range from 0.01 to 0.1 M. In both variations, the column may be regenerated with a relatively concentrated salt solution, e.g. 2 M NaCl.

As an alternative to the above-described process employing PEG-induced crystallization of RuBisCO, it has been found that substantially pure RuBisCO may be separated from a fractionated mixture of proteins without prior crystallization. Using this approach, the crystallization step is simply omitted and the mixture applied directly to the ion-exchange resin.

The following examples are included to demonstrate the effectiveness of the method and are not to be construed so as to limit in any manner the nature or scope of the method or the appended claims.

EXPERIMENTAL

Experiment One

Ryegrass tillers (56 g) are homogenized in 120 ml of distilled water at 4° C. Sodium meta-bisulfite was added to a final concentration of approximately 0.01 M. The leaves were then ground into solution (an additional 20 ml of water was added during grinding) and filtered. Considerable foaming occurred during filtering. PEG (63 ml) and 2 M $MgCl_2$ (2.85 ml unbuffered solution) were added to the filtrate. The resulting mixture was centrifuged at 7,000 rpm for 15 minutes. After discarding the pellet, PEG (3.75 gm) was added to the supernatant and the mixture stored in a refrigerator for 16 hours. At the end of that time, microcrystals were observed formed at the bottom of the beaker. The supernatant was then discarded and the crystals washed, dissolved in water and thereafter lyophilized to obtain 240 mg of a white powder material (no odor) which was then stored under refrigeration.

Seven days later, approximately 15 mg of the white powder was dissolved in distilled water (3.5 ml). The resulting solution was passed through a column (1.6×30) containing DEAE-cellulose (DEAE-52) equilibrated with water. The column was then washed with (1) approximately 300 ml of water, (2) a solution of 30 mM $MgCl_2$ and water (without buffer), (3) 60 mM $MgCl_2$ (no buffer), and (4) 2 M NaCl solution in water.

Peaks occurred during the initial water wash and during both washes with $MgCl_2$. The peak fractions were assayed, revealing that no RuBisCO was eluted during the water wash, i.e., only contaminants were eluted, while approximately equal amounts of RuBisCO were eluted during both of the $MgCl_2$ washes.

Experiment Two

Destemmed alfalfa (67 g) was added to 130 ml of distilled water. Sodium meta-bisulfite was added to a final concentration of approximately 0.01 M. The leaf material was ground and PEG (70 ml) and 2 M $MgCl_2$ (3 ml) were added to the suspension. After centrifuging to remove the membranes and organelles, additional PEG (3.8 gm) was added in two increments to the supernatant. After refrigeration for several hours, microcrystal formation was observed.

The crystals were then washed and dissolved in distilled water (10 ml). The solution was centrifuged to remove debris and the supernatant (approximately 7.5 ml) was passed through a column packed with DEAE-cellulose (DEAE-52) at 4° C. equilibrated with water. The column was then washed with distilled water (200 ml) and a small peak was observed. A second wash with 60 mM $MgCl_2$ in water (150 ml) yielded a large peak. A final wash with 2 M NaCl yielded a third peak. The material from each peak was collected and an assay revealed that only the second peak contained RuBisCO.

Experiment Three

Destemmed alfalfa leaves (72 g) were placed in deionized water (140 ml, 4° C.). Sodium meta-bisulfite was added to a final concentration of approximately 0.02 M and the leaves were comminuted to form a suspension. PEG (80 ml) and 2 M $MgCl_2$ (3.3 ml) were added to the suspension which was then centrifuged to remove the remaining plant material. The supernatant was filtered through one layer of Miracloth to remove the remaining floating debris. PEG (2.1 gm) was added and allowed to dissolve completely. Additional PEG (2.1 gm) was added and the solution became cloudy. After storing at 4° C. for approximately two hours, microcrystalline material was observed. After storing overnight at 4° C., a substantial amount of microcrystalline material was aggregated at the bottom of the beaker. The crystals had various shapes with the largest dimension not exceeding 25 mm. Most of the supernatant was decanted and crytals were resuspended in the remaining solution which was then centrifuged. The pellet of crystalline material was washed with unbuffered PEG solution (15%), centrifuged again with the newly formed pellet being dissolved in distilled water.

The solution (5.2 ml) was passed through a column having DEAE-cellulose packing (DEAE-52) equilibrated with distilled water. The column was then washed with distilled water (350 ml) producing a first peak. The column was next washed with unbuffered 60 mM $MgCl_2$ (approximately 150 ml) producing a second peak. Finally, the column was washed with unbuffered 2 M NaCl to produce a third peak.

Peak one revealed no protein activity. Peak two was active. Peak three was several hundred counts about background. Approximately 80% of the activity was recovered in peak two.

Experiment Four

Destemmed alfalfa leaves (0.5 g) were added to distilled water with sodium meta-bisulfite (approximately 0.02 M). The leaves were comminuted and the solution centrifuged to remove the solid plant material. The supernatant was placed in a water bath (37°–40° C.) and the solution allowed to equilibrate. After the solution reached 37°–40° C., it was left for an additional 10 minutes and then removed. The solution was then centrifuged and the pellet discarded. The supernatant was passed through a DEAE-cellulose (DEAE-52) column at room temperature equilibrated with water. The column was rinsed with distilled water until the peak returned to base line. The column was then washed with 0.6 M $MgCl_2$ until the second peak returned to base line. Finally the column was washed with 2 M NaCl. Assay and gel electrophoresis revealed the second peak to be substantially pure RuBisCO.

Experiment Five

Destemmed Alfalfa leaves (50 g) were placed in distilled water (100 ml) and sodium meta-bisulfite added to a concentration of 0.01 M. The leaves were comminuted in a blender and the suspension heated to 40° C. for 10 minutes. The suspension was then centrifuged (10,000 rpm for 10 minutes) and the pellet discarded. The supernatant was passed through a DEAE-cellulose (DEAE-52) column equilibrated with water. The column was then washed with distilled water (approximately 200 ml) to obtain a first peak. After removing the top 0.5 cm of the column material, where a green and yellow band had been deposited, the column was washed with 0.06 M $MgCl_2$ (200 ml) to obtain a second peak. The column was then washed with 2 M NaCl to obtain a small third peak. Assay revealed the first peak to contain a small amount of RuBisCO and the second peak to contain substantially pure RuBisCO.

Although the foregoing invention has been described in some detail by way of illustration and example for purposes of clarity of understanding, it will be obvious that certain changes and modifications may be practiced within the scope of the appended claims.

What is claimed is:

1. A method for preparing ribulose 1,5-bisphosphate carboxylase (RuBisCO) from plant material, said method comprising:
   comminuting the plant material in an aqueous solution to form a suspension;
   fractionating said suspension to release the RuBisCO from the ground plant material into the solution; and
   adding a sufficient amount of polyethylene glycol (PEG) to the solution so that crystals of RuBisCO are selectively formed, said crystals having impurities separating the crystals from the solution; redissolving the crystals in water;
   passing the redissolved crystals through an anionic resin bed;
   washing the column to remove the unbound material; and
   passing a single solution containing predetermined concentration of a divalent metal ion through the column at a concentration sufficient to selectively elute the RuBisCO from the resin.

2. A method as in claim 1, further comprising separating the crystals from the solution and lyophilizing the crystals.

3. A method as in claim 1, wherein said fractionating step comprises adding at least one of dextrans, polymeric alcohols, and ammonium sulfate to the suspension at a concentration effective to release the RuBisCO from the plant material.

4. A method as in claim 1, wherein said fractionating step comprises heating the suspension at a sufficient temperature and for a sufficient time to release the RuBisCO from the plant material.

5. A method as in claim 1, wherein the concentration of divalent metal ion is in the range from 0.01 to 0.1 M.

6. A method for preparing ribulose 1,5-bisphosphate carboxylase (RuBisCO) from plant material, said method comprising:
   comminuting the plant material in an aqueous solution to form a suspension;
   fractionating said suspension to release the RuBisCO from the ground plant material into the solution; and
   adding a sufficient amount of polyethylene glycol (PEG) to the solution so that crystals of RuBisCO are selectively formed;
   separating the crystals from the solution;
   redissolving the crystals in substantially pure water; and
   passing the redissolved crystals through an anionic resin bed in the presence of a divalent metal ion at a concentration sufficient to prevent the binding of RuBisCO to the resin.

7. A method as in claim 6, wherein the concentration of divalent metal ion is in the range from 0.01 to 0.1 M.

8. A method as in claim 6, further including the step of collecting the eluent from the resin bed and separating the purified RuBisCO therefrom.

9. A method for preparing ribulose 1,5-bisphosphate carboxylase (RuBisCO) from plant material, said method comprising:
comminuting the plant material in an aqueous solution to form a suspension;
fractionating said suspension to release the RuBisCO from the comminuted plant material into the solution;
separating the remaining plant material from the solution to form a supernatant;
passing the supernatant through an anionic resin bed so that at least the RuBisCO binds to said resin;
washing the resin bed to remove unbound material; and
passing a solution including divalent metal ion through the resin bed to specifically elute the RuBisCO from the resin.

10. A method for preparing ribulose 1,5-bisphosphate carboxylase (RuBisCO) from plant material, said method comprising:
comminuting the plant material in an aqueous solution to form a suspension;
fractionating said suspension to release the RuBisCO and proteinaceous contaminants from the comminuted plant material into the solution;
separating the remaining plant material from the solution to form a supernatant including the RuBisCO and at least some of said dissolved contaminants;
passing the supernatant through an anionic resin bed in the presence of a divalent metal ion at a concentration selected so that substantially all of the contaminants bind to resin while the RuBisCO is prevented from binding to said resin.

11. A method for purifying a solution of 1,5-bisphosphate carboxylase (RuBisCO) from plant material, said method comprising:
passing the solution through an anionic resin bed;
selectively applying a divalent metal ion to the resin bed at a concentration in the range from 0.01 to 0.1 M to elute the RuBisCO from the column while allowing the contaminants to remain bound.

12. A method as in claim 11, wherein the divalent metal ion is applied simultaneously with the passing of the solution so that binding of RuBisCO to the resin is prevented.

13. A method as in claim 11, wherein the divalent metal ion is applied after the RuBisCO has become bound to the resin.

14. A method as in claim 11, wherein the anionic resin bed is diethylaminoethyl (DEAE) cellulose.

* * * * *